(12) United States Patent
Niederbacher

(10) Patent No.: US 12,415,977 B2
(45) Date of Patent: Sep. 16, 2025

(54) PLUG FLOW FERMENTER FOR A BIOGAS PLANT

(71) Applicant: Michael Niederbacher, Bruneck (IT)

(72) Inventor: Michael Niederbacher, Bruneck (IT)

(*) Notice: Subject to any disclaimer, the term of this patent is extended or adjusted under 35 U.S.C. 154(b) by 652 days.

(21) Appl. No.: 17/759,658

(22) PCT Filed: Jan. 20, 2021

(86) PCT No.: PCT/EP2021/051127
§ 371 (c)(1),
(2) Date: Jul. 28, 2022

(87) PCT Pub. No.: WO2021/151746
PCT Pub. Date: Aug. 5, 2021

(65) Prior Publication Data
US 2023/0066584 A1    Mar. 2, 2023

(30) Foreign Application Priority Data
Jan. 30, 2020  (DE) .................. DE102020102264.6

(51) Int. Cl.
| | |
|---|---|
| *C12M 1/107* | (2006.01) |
| *C12M 1/00* | (2006.01) |
| *C12M 1/06* | (2006.01) |
| *C12M 1/34* | (2006.01) |
| *C12M 1/36* | (2006.01) |

(52) U.S. Cl.
CPC ............ *C12M 21/04* (2013.01); *C12M 27/02* (2013.01); *C12M 27/18* (2013.01); *C12M 41/40* (2013.01); *C12M 41/42* (2013.01); *C12M 41/48* (2013.01)

(58) Field of Classification Search
CPC ...... C12M 21/04; C12M 27/02; C12M 27/18; C12M 41/40; C12M 41/42; C12M 41/48; C12M 41/00; Y02E 50/30
See application file for complete search history.

(56) References Cited

U.S. PATENT DOCUMENTS

2012/0009664 A1* 1/2012 Buerger ............... C12M 41/44
435/286.5

FOREIGN PATENT DOCUMENTS

| DE | 202009005024 U1 * | 10/2009 | .......... B01F 7/00733 |
| EP | 2213720 A1 * | 8/2010 | .......... B01F 7/00741 |

* cited by examiner

*Primary Examiner* — Michael L Hobbs
(74) *Attorney, Agent, or Firm* — Southeast IP Group LLC; Thomas L. Moses

(57) ABSTRACT

The invention relates to a fermenter vessel (1) of a biogas plant, having at least one height-adjustable agitator (8), wherein the agitator (8), in the fermenter vessel (1), is guided with a guide element (17) on a guide rail (9) oriented approximately vertically in a vertical axis direction and is held in height-adjustable fashion by means of a traction cable (10). According to the invention, a traction force measuring device (22; 25) is provided for directly and/or indirectly measuring the traction force on the traction cable (10) in accordance with a cable tension, such that, by means of the traction force measuring device (22; 25), in the case of a preferably controlled height adjustment of the agitator (8), varying traction force measurement signals are generated in accordance with varying traction forces and are supplied to an evaluation device (20).

17 Claims, 2 Drawing Sheets

PLUG FLOW FERMENTER FOR A BIOGAS PLANT

FIELD OF THE INVENTION

Figure 1:
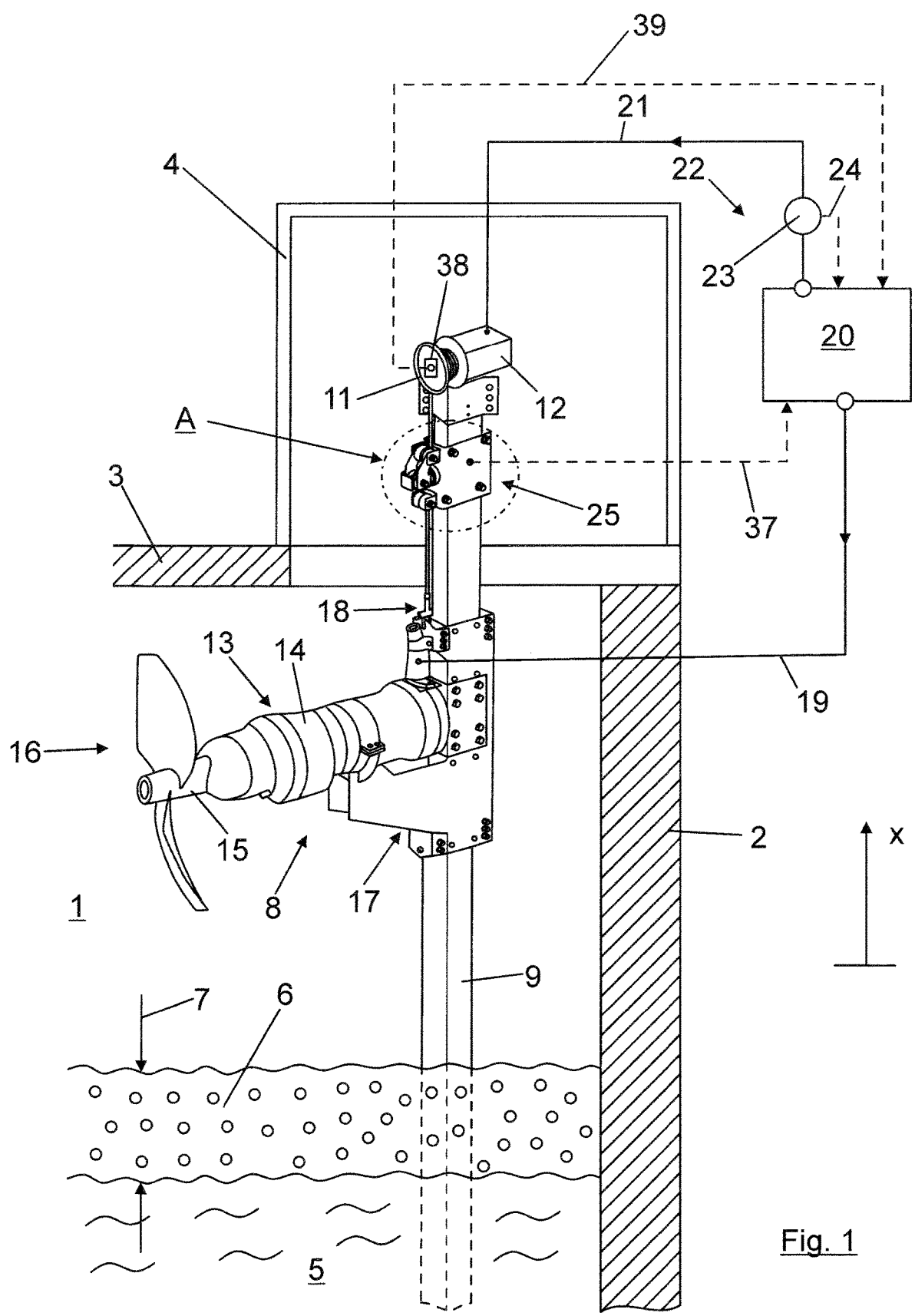

The invention relates to a fermenter vessel of a biogas plant having at least one height-adjustable agitator according to the preamble of claim 1, and to a method for operating a fermenter vessel according to the preamble of claim 17.

BACKGROUND OF THE INVENTION

In a known fermenter vessel of the type in question of a biogas plant (DE 10 2007 009 451 A1), an agitator is held as a submersible motor agitator with guide elements on a vertical guide rail and is held in a height-adjustable fashion by means of a traction cable on a stationary cable pulley in the upper guide rail region. The agitator is height-adjustable by winding or unwinding the cable with a controllable cable pulley motor drive as a height actuator.

In addition, a fill level measuring device is provided here, by means of which a fill level of a substrate is detected and a corresponding fill level measurement signal is generated as the actual height value signal. In addition, a control unit is provided, which is supplied with the fill level measurement signal, wherein a height actuator for the submersible motor agitator is controlled such that, if necessary, it is lowered to the extent that the agitator blades of the submersible motor agitator are completely immersed in the substrate. Neither a shutdown of the cable pulley motor drive or of the height actuator at a lower or upper end position of the agitator, nor a recognition and detection of a floating or sinking layer and, if appropriate, of its thickness is thus possible.

SUMMARY OF THE INVENTION

The object of the invention is to further develop a fermenter vessel of the type in question of a biogas plant having at least one height-adjustable agitator in such a way that a height adjustment of the agitator can be carried out in a functionally reliable manner with relatively little effort and relatively simple measures.

This object is achieved with the features of the independent claims.

According to claim 1, a fermenter vessel of a biogas plant having at least one height-adjustable agitator is provided, wherein the agitator, in the fermenter vessel, is guided with a guide element on a guide rail oriented approximately vertically in a vertical axis direction and is held in height-adjustable fashion by means of a traction cable. According to the invention, a traction force measuring device is provided for directly and/or indirectly measuring the traction force on the traction cable in accordance with a cable tension, such that, by means of the traction force measuring device, in the case of a preferably controlled height adjustment of the agitator, varying traction force measurement signals are generated in accordance with varying traction forces and are supplied to an evaluation device.

This makes it possible to realize a shutdown of the height adjustment at end positions of the agitator and/or to determine heights and/or thicknesses and/or consistencies of floating and/or sinking layers in the substrate and, if necessary, to adapt measures in the plant control, in particular height positions, directional positions, run times and rotational speeds, etc. of one or more submersible motor agitators in a suitable manner to the fermentation process based on this information.

According to a particularly preferred embodiment, it is proposed that the agitator be held in a height-adjustable fashion on a cable pulley by means of the traction cable, wherein the agitator is height-adjustable by winding or unwinding the traction cable with a controllable cable pulley motor drive as a height actuator. At least one traction force threshold value is predefined in the evaluation device; the cable pulley motor drive shuts down automatically when said threshold value is reached. If, for example, a lower predetermined stop point in the fermenter vessel is reached during a lowering process of the agitator, or if the agitator coming from above hits a floating or sinking layer with a particularly high consistency, the traction force on the traction cable downward decreases greatly according to the reduced cable tension, and the cable pulley motor drive is automatically shut down by the evaluation device.

Accordingly, the shutdown function can, if appropriate, take place with a fault notification even when the height of the agitator is adjusted upward, if a predetermined upper stop on the guide rail or a largely impermeable floating or sinking layer is reached from below, causing the cable tension to increase.

When passing downward or upward through a sinking or floating layer through which the agitator can still pass without a fault function and without being shut down, both the thickness and consistency of a sinking or floating layer may be determinable, if applicable, as a result of the local reduction or increase in the cable tension during passage.

Simple shutdown processes in conjunction with high changes in cable tension can optionally be realized via simple limit switches and fixed wiring without complex evaluations having to be carried out in preferably programmable digital controls.

An evaluation device for evaluating measured cable tension signals can regularly be easily integrated into a plant control for the biogas plant that is usually present anyway.

According to a particularly preferred embodiment, the cable pulley is arranged in a stationary manner on the fermenter vessel, preferably arranged on an upper guide rail region of the guide rail. The stationary arrangement in particular on the upper guide rail region brings about good accessibility and favorable geometric conditions with respect to the cable guidance to the agitator.

In a preferred embodiment of the invention, the traction force measuring device is part of the controllable cable pulley motor drive, wherein a current traction force measurement signal or cable tension measurement signal is generated by measuring an actuator energy consumed by the cable pulley motor drive during a height adjustment, preferably taking into account the actuating direction downward or upward, which measurement signal is then evaluated in the evaluation device, if appropriate, for further measures.

Preferably, an electric motor drive is used here as a controllable cable pulley motor drive, wherein a current measuring device, preferably an ammeter, is provided by means of which current consumption is measured during a height adjustment for generating a current traction force measurement signal and is supplied to the evaluation device.

Further, alternatively or redundantly, a different traction force measuring device can be used, which may be arranged, for example, in a stationary manner in the region of the guide rail and/or, for example, below a cable pulley. Such a traction force measuring device preferably has a deflection device with at least one deflection element for the traction cable from its vertical tension direction, as a result of which a transverse force originating from the traction cable on the at least one deflection element is generated according to a current cable tension. The higher the traction force and thus the cable tension, the higher the transverse force resulting from the deflection. This transverse force is measured with a sensor element and supplied as a traction force measurement signal to an evaluation device.

In a preferred specific embodiment, the deflection device comprises a plurality of deflection rollers as deflection elements, preferably three deflection rollers in a triangular arrangement, wherein an—in relation to the vertical axis direction—upper deflection roller and a lower deflection roller are located with contact surfaces in the vertical cable tension direction. A central deflection roller is arranged, preferably in an axially parallel manner, between the upper and the lower deflection roller in a manner offset in the transverse direction and movably guided. The traction cable is guided opposite the contact surfaces of the upper deflection roller and the lower deflection roller about the central deflection roller, so that, when a load is exerted on the cable, the central deflection roller is pushed in the direction of the vertical cable tension direction with a horizontal transverse force due to its transverse offset. Preferably, the traction force measuring device has a pressure sensor as sensor element, which pressure sensor is connected with its pressure-sensitive surface to the mounting of the central deflection roller for measuring its transverse force and generating a traction force measurement signal, wherein it is preferably provided for the pressure sensor to be fastened and/or supported in a stationary manner on the deflection device.

Such a traction force measuring device is functionally reliable, relatively simply structured and inexpensive to produce.

According to an advantageous embodiment variant, the mounting and movable transverse guidance of the central deflection roller can be easily carried out by means of a rocker arm which is fastened pivotably in the direction of the pressure sensor to the deflection device, preferably to a bearing block of the upper deflection roller. For a particularly stable arrangement, the rocker arm is designed as a fork arm with two fork parts spaced apart from one another, between which the central deflection roller is arranged with its axis. Furthermore, a cover, for example as a securing plate, can advantageously be attached to the outer side of the central deflection roller, which cover can be connected to the rocker arm in order to prevent the traction cable from falling off the central deflection roller when it is not under tension.

The sensor element as the pressure sensor can be used in the manner of commercially available weighing cells which are available on the market as piezoresistive pressure sensors, in particular with strain gauges or as piezoelectric pressure sensors or as inductive pressure sensors or as capacitive pressure sensors.

In a further embodiment, it is proposed that a rotational speed sensor be arranged on the cable pulley and/or on the cable pulley motor drive, by means of which rotational speed sensor the current number of cable windings and thus the currently unwound cable length can be measured in conjunction with the current height position of the agitator. A height position signal generated therewith can be evaluated in the evaluation device for a position determination and/or thickness determination of floating and/or sinking layers.

According to a particularly preferred embodiment, varying traction force measurement signals can thus be suppliable to the evaluation device for determining the height position and/or the thickness and/or the consistency of a floating layer and/or sinking layer in the substrate, wherein it is preferably provided that the information obtained in this way with respect to the height position and/or the thickness and/or the consistency of a floating layer and/or sinking layer in the substrate is supplied to a plant control for the biogas plant and is taken into account and/or shown on a display as a control parameter when controlling the biogas plant, in particular when controlling the agitator.

Furthermore, submersible motor agitators known per se can be used as one or more agitators with a preferably electric or hydraulic or pneumatic agitator motor in a tubular housing, from which an agitator shaft with a propeller with at least one agitator blade projects axially on one side. Even though this is the preferred embodiment, the term agitator is expressly to be understood in a broad sense in all embodiments of this invention and is therefore intended to include any type of submersible device which serves for generating flow, i.e., expressly also submersible devices without agitator blades, such as, for example, submersible pumps.

In addition, a guide carriage encompassing the guide rail or a guide carriage engaging therein can be arranged as a guide element opposite the agitator blades, to which guide carriage the tubular housing is fastened and the traction cable is connected.

The advantages achievable with the method according to the invention correspond to those of the fermenter vessel. In this respect, reference is made to the previous statements in order to avoid repetitions.

BRIEF DESCRIPTION OF THE INVENTION

The invention is explained in more detail only by way of example based on a drawing.

Figure 2:
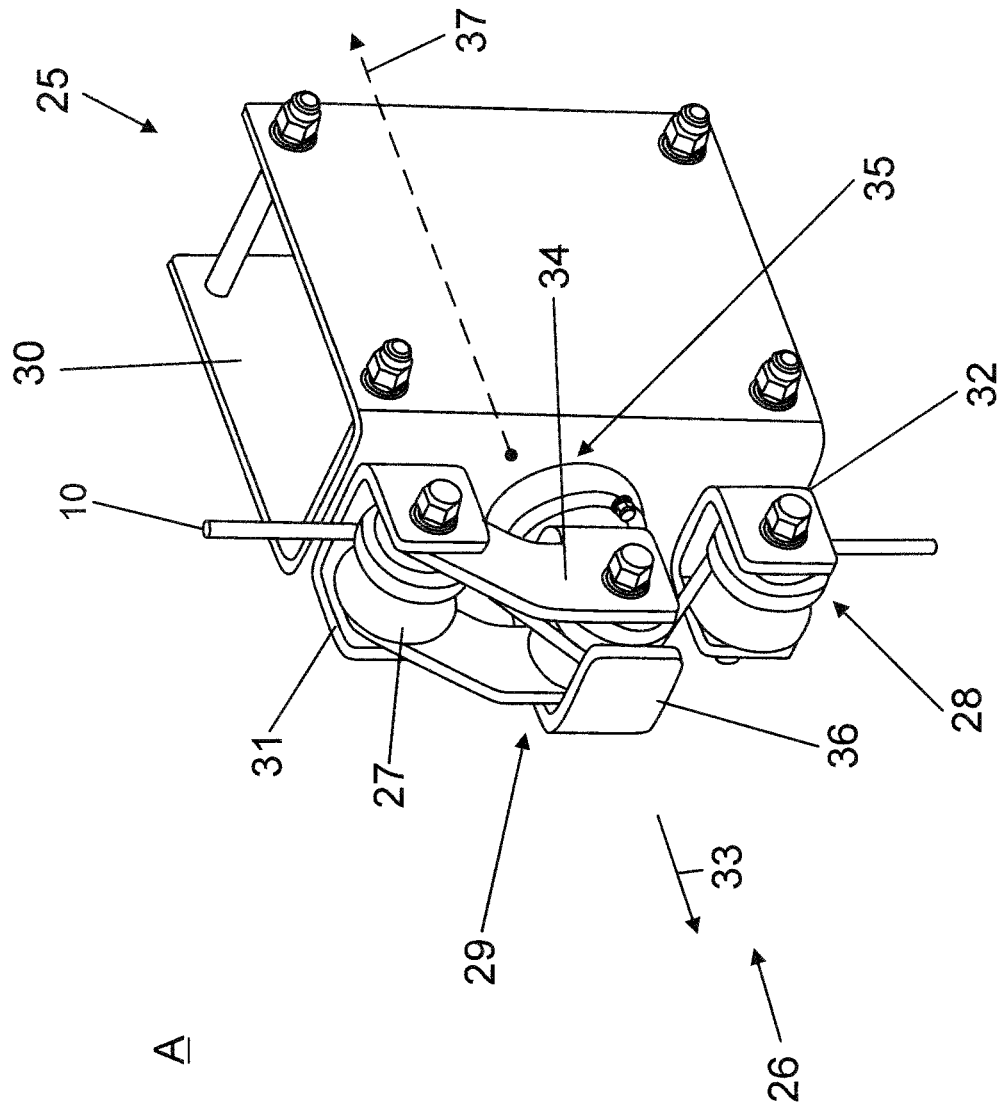

In the drawing:

FIG. 1 shows a schematic representation of a fermenter vessel of a biogas plant having at least one height-adjustable agitator, and FIG. 2 shows an enlarged representation of a traction force measuring device at position A of FIG. 1.

DETAILED DESCRIPTION OF THE INVENTION

FIG. 1 shows, in a highly schematic manner, an upper partial region of a fermenter vessel 1 of a biogas plant with a portion of an upper region of an outer wall 2 of a film wall or ceiling wall 3 and a service shaft 4 mounted in a gas-tight manner as a covering hood above a film cut-out or ceiling cut-out. The fermenter vessel 1 is filled up to an upper region with a substrate 5 made of liquid biomass, wherein a floating layer 6 having a relatively dense consistency and a thickness 7 has already formed here. An agitator as a submersible motor agitator 8 is held in the fermenter vessel 1 in a side region on a guide rail 9 oriented approximately vertically in a vertical axis direction x by means of a traction cable 10 on a stationary cable pulley 11 in the upper guide rail region. The submersible motor agitator 8 is held on the guide rail 9 in a height-adjustable fashion by winding or unwinding the traction cable 10 by means of a controllable electric cable pulley motor drive 12.

The guide rail 9 is pivotably mounted about its axis, on the one hand, in the film region or ceiling region or in the region of the service shaft 4 and, on the other hand, on the base (not shown) of the fermenter vessel 1, wherein these bearing points are designed in a conventional manner and are therefore not shown in detail.

The submersible motor agitator 8 is equipped with an electric agitator motor 13 in a tubular housing 14, from which an agitator shaft 15 with a propeller 16, which in this case has two blades only by way of example, projects axially on one side. A guide carriage 17 encompassing the guide rail 9 is arranged opposite the propeller 16 as a guide element, to which both the tubular housing 14 and the lower end of the traction cable 10 are connected at a connection point 18. The electrical energy for the electric agitator motor 13 is supplied in a controlled/regulated manner by means of a schematically indicated power line 19 of a control device 20.

In this case, the cable pulley motor drive 12 is also an electric motor drive and is supplied with current as actuator energy via the control device 20 and a power line 21.

In order to realize a traction force measuring device 22 for indirectly measuring the traction force on the traction cable 10 according to a cable tension, the current consumption of the cable pulley motor drive 12 is measured during a height adjustment by means of a (schematically shown) ammeter or current measuring device 23 and is supplied to the control device 20 via a signal line 24. The control device 20 contains an evaluation device in which one or more traction force threshold values can be predetermined; power supply to the cable pulley motor drive 12 is interrupted automatically when said threshold value(s) is/are reached. In addition, varying traction force measurement signals for determining the height position and/or the thickness 7 and/or the consistency of a floating layer 6 or a sinking layer in the substrate 5 can be analyzed and evaluated in the evaluation device, which are then taken into account in particular when controlling the agitator. This information can optionally also be shown on a display (not shown).

Moreover, in FIG. 1, a further alternative or optionally additional and hence redundant traction force measuring device 25 is drawn in region A which is encircled by a dot-dash line. The alternative or additional traction force measuring device 25 is explained in more detail with reference to the enlarged illustration in FIG. 2:

Here, the traction force measuring device 25 is arranged, for example, in a stationary manner in the upper region of the guide rail 9 below the cable pulley 11 and has a deflection device 26 with at least three deflection rollers in the example shown here, namely an upper deflection roller 27, a lower deflection roller 28 and a central deflection roller 29. In the example shown here, the deflection rollers 27, 28 and 29 are thus arranged in a triangular arrangement. Here, by way of example, the traction force measuring device 25 is fastened with a clamping housing 30 to the guide rail 9 so as to be non-displaceable. As shown by way of example here, a bearing block 31 for the upper deflection roller 27 and a bearing block 32 for the lower deflection roller 28 can be arranged on the front wall of the clamping housing 30, wherein the traction cable 10 is guided vertically at the rear side from above onto the upper deflection roller 27 and extends again vertically downward from the lower deflection roller 28.

As shown merely by way of example here, the central deflection roller 29 can have the same dimensions as the upper deflection roller 27 and/or the lower deflection roller 28.

In the specific example shown here, the central deflection roller 29 is arranged in an axially parallel manner offset to the front in the transverse direction (indicated schematically by arrow 33). The central deflection roller 29 is mounted on a rocker arm, which is designed here as a fork arm 34 merely by way of example, which rocker arm is tied or connected pivotably to the bearing block 31 so that the central deflection roller 29 is held movably in the transverse direction by means of the fork arm 34.

The traction cable 10 is shown to be guided from the rear side of the upper deflection roller 27 forward via the central deflection roller 29 and from there back again via the rear side of the lower deflection roller 28, as a result of which a transverse force results in the direction of the clamping housing 30 due to the transverse offset of the central deflection roller 29 when a tensile load is applied to the traction cable 10. This transverse force is measured by means of a (commercially available) pressure sensor 35 (not shown in more detail) as a measure of the tension of the traction cable 10, wherein, on the one hand, the pressure sensor 35 is supported on and fastened to the clamping housing 30 and, on the other hand, the mounting of the central deflection roller 29 in accordance with the fork arm 34 rests with a fork arm part on the pressure-sensitive surface of the pressure sensor 35 or is connected there. As can be seen, the arrangement is designed such that a transverse force acts as perpendicularly as possible on the pressure-sensitive surface of the pressure sensor 35.

Furthermore, a securing element 36 is formed on the fork arm 34 as a bent sheet metal part, which covers an outer region of the central deflection roller 29 so that a relaxed traction cable 10 cannot fall off the central deflection roller 29.

A pressure signal generated with the pressure sensor 35 and corresponding to a traction force measurement signal on the traction cable 10 is supplied to the control device 20 with a signal line 37 and is evaluated there, as a result of which control measures are possibly initiated or adapted, as already described above in connection with the first embodiment of a traction force measuring device 22.

In a further embodiment, a rotational speed sensor 38 is arranged on the cable pulley motor drive 12 or here on the cable pulley 11, by means of which the current number of cable windings on the cable pulley 11 and thus the currently unwound cable length is measured in conjunction with the current height position of the submersible motor agitator 8. A corresponding rotational speed signal or height position signal is supplied to the control device 20 with the signal line 39, which control device can take control measures also taking into account the height position of the submersible motor agitator 8.

LIST OF REFERENCE SIGNS

1 Fermenter vessel
2 Outer wall
3 Film wall or ceiling wall
4 Service shaft
5 Substrate
6 Floating layer
7 Thickness
8 Submersible motor agitator
9 Guide rail
10 Traction cable
11 Cable pulley
12 Cable pulley motor drive
13 Electric agitator motor
14 Tubular housing
15 Agitator shaft
16 Propeller
17 Guide carriage
18 Connection point
19 Power line
20 Control device
21 Power line
22 Traction force measuring device 23 Current measuring device
24 Signal line
25 Traction force measuring device
26 Deflection device
27 Upper deflection roller
28 Lower deflection roller
29 Central deflection roller
30 Clamping housing
31 Bearing block
32 Bearing block
33 Arrow
34 Fork arm
35 Pressure sensor
36 Securing element
37 Signal line
38 Rotational speed sensor
39 Signal line

The invention claimed is:

1. A fermenter vessel of a biogas plant comprising:
at least one height-adjustable agitator, wherein the agitator in the fermenter vessel, is guided with a guide element on a guide rail oriented approximately vertically in a vertical axis direction and is held in height-adjustable fashion by means of a traction cable;
a traction force measuring device is provided for measuring the traction force on the traction cable in accordance with a cable tension, such that, by means of the traction force measuring device, in the case of a controlled height adjustment of the agitator, varying traction force measurement signals are generated in accordance with varying traction forces and are supplied to an evaluation device.

2. The fermenter vessel according to claim 1, wherein the agitator is held in height-adjustable fashion on a cable pulley by means of the traction cable,
the agitator is height-adjustable by winding or unwinding the traction cable with a controllable cable pulley motor drive as a height actuator, and
at least one traction force threshold value is predefined in the evaluation device, wherein the cable pulley motor drive shuts down automatically when said threshold value is reached.

3. The fermenter vessel according to claim 2, wherein the cable pulley is arranged in a stationary manner on the fermenter vessel, on an upper guide rail region of the guide rail.

4. The fermenter vessel according to claim 2, wherein
the traction force measuring device is part of the controllable cable pulley motor drive, and
an actuator energy measuring unit is provided, by means of which an actuator energy consumed by the cable pulley motor drive during a height adjustment is measured and a current traction force measurement signal is respectively derived therefrom, taking into account the actuating direction downward or upward.

5. The fermenter vessel according to claim 2, wherein
the controllable cable pulley motor drive is an electric motor drive, and
a current measuring device, is provided by means of which current consumption is measured during a height adjustment for generating a current traction force measurement signal and is supplied to the evaluation device.

6. The fermenter vessel according to claim 1, wherein the traction force measuring device is arranged preferably in a stationary manner in the region of the guide rail, wherein the traction force measuring device is positioned below the cable pulley in relation to the vertical axis direction.

7. The fermenter vessel according to claim 1, wherein characterized in that
the traction force measuring device has a deflection device with at least one deflection element for the traction cable from its vertical clamping direction, and
a sensor element is provided, by means of which the resulting transverse force on the at least one deflection element is measured and supplied to the evaluation device as a traction force measurement signal for the cable tension.

8. The fermenter vessel according to claim 7, wherein
the deflection device comprises a plurality of deflection rollers as deflection elements, at least three deflection rollers in a triangular arrangement, wherein, in relation to the vertical axis direction, upper deflection roller and a lower deflection roller are located with contact surfaces in the vertical cable tension direction, and
a central deflection roller is arranged, in an axially parallel manner, between the upper deflection roller and the lower deflection roller in a manner offset in the transverse direction and movably guided, and the traction cable is guided opposite the contact surfaces of the upper deflection roller and the lower deflection roller about the central deflection roller, so that, when a load is exerted on the cable, the central deflection roller is pushed in the direction of the vertical cable tension direction with a horizontal transverse force.

9. The fermenter vessel according to claim 8, wherein the traction force measuring device has a pressure sensor as sensor element, which pressure sensor is connected with its pressure-sensitive surface to the mounting of the central deflection roller for measuring its transverse force and generating a traction force measurement signal, wherein it is preferably provided for the pressure sensor to be fastened and/or supported in a stationary manner on the deflection device.

10. The fermenter vessel according to claim 8, wherein the mounting and movable transverse guidance of the central deflection roller is carried out by means of a rocker arm which is fastened pivotably in the direction of the pressure sensor to the deflection device to a bearing block of the upper deflection roller.

11. The fermenter vessel according to claim 10, wherein the rocker arm is designed as a fork arm with two fork parts spaced apart from one another, between which the central deflection roller is arranged with its axis.

12. The fermenter vessel according to claim 7, wherein the sensor element is selected from the group consisting of a pressure sensor in the manner of a weighing cell as a piezoresistive pressure sensor, with strain gauges, a piezoelectric pressure sensor, an inductive pressure sensor, and a capacitive pressure sensor.

13. The fermenter vessel according to claim 2, wherein a rotational speed sensor is arranged on the cable pulley and/or on the cable pulley motor drive, by means of which the current number of cable windings on the cable pulley and thus the currently unwound cable length can be measured in conjunction with the current height position of the agitator, so that a height position signal generated therewith is supplied to the evaluation device for determining the position and/or thickness of floating and/or sinking layers.

14. The fermenter vessel according to claim 1, wherein, varying traction force measurement signals are supplied to the evaluation device for determining the height position and/or the thickness and/or the consistency of a floating layer and/or sinking layer in the substrate, wherein the information obtained in this way with respect to the height position and/or the thickness and/or the consistency of a floating layer and/or sinking layer in the substrate is supplied to a plant control for the biogas plant and is taken into account and/or shown on a display as a control parameter when controlling the biogas plant when controlling the agitator.

15. The fermenter vessel according to claim 1, wherein the evaluation device is integrated into a plant control for the biogas plant.

16. The fermenter vessel according to claim 1, wherein
   the agitator is a submersible motor agitator having an agitator motor that is selected from the group consisting of an electric motor agitator, a hydraulic agitator motor, and a pneumatic agitator motor in a tubular housing, from which an agitator shaft with a propeller with at least one agitator blade projects axially on one side, and
   a guide carriage encompassing the guide rail or engaging therein is arranged as a guide element opposite the propeller, to which guide carriage the tubular housing is fastened and the lower end of the traction cable is connected.

17. A method for operating a fermenter vessel of a biogas plant comprising the steps of
   providing at least one height-adjustable agitator,
   guiding the agitator in the fermenter vessel with a guide element on a guide rail that is oriented approximately vertically in a vertical axis direction and is held in height-adjustable fashion by means of a traction cable;
   providing a traction force measuring device for measuring the traction force on the traction cable in accordance with a cable tension, such that, by means of the traction force measuring device, in the case of a controlled height adjustment of the agitator, varying traction force measurement signals are generated in accordance with varying traction forces and are supplied to an evaluation device.

* * * * *